United States Patent
Qian et al.

(10) Patent No.: US 7,541,463 B2
(45) Date of Patent: Jun. 2, 2009

(54) SULFUR-CONTAINING NAPHTHALIMIDE DERIVATIVES

(75) Inventors: Xuhong Qian, Shanghai (CN); Yonggang Li, Shanghai (CN); Yufang Xu, Shanghai (CN); Jian Ding, Shanghai (CN); Liping Lin, Shanghai (CN); Zehong Miao, Shanghai (CN); Hong Zhu, Shanghai (CN); Baoyuan Qu, Shanghai (CN)

(73) Assignees: East China University of Science and Technology, Shanghai (CN); Shanghai Institute of Materia Medica, Chinese Academy of Science, Shanghai (CN); Dalian University of Technology, Dalian (CN)

( * ) Notice: Subject to any disclaimer, the term of this patent is extended or adjusted under 35 U.S.C. 154(b) by 235 days.

(21) Appl. No.: 11/263,591

(22) Filed: Oct. 31, 2005

(65) Prior Publication Data

US 2006/0111367 A1      May 25, 2006

Related U.S. Application Data

(63) Continuation of application No. PCT/CN2004/000442, filed on Apr. 30, 2004.

(30) Foreign Application Priority Data

Apr. 30, 2003    (CN)    ................. 03 1 16709

(51) Int. Cl.
*A61K 31/4365* (2006.01)
*C07D 221/18* (2006.01)
*C07D 471/06* (2006.01)

(52) U.S. Cl. ............................. 546/58; 546/66; 546/67; 514/280; 514/285; 514/287

(58) Field of Classification Search .................. 546/58, 546/66, 67; 514/280, 285, 287
See application file for complete search history.

(56) References Cited

U.S. PATENT DOCUMENTS

| | | | |
|---|---|---|---|
| 3,888,863 | A | 6/1975 | Troster |
| 4,254,109 | A | 3/1981 | Sestanj |

FOREIGN PATENT DOCUMENTS

| | | |
|---|---|---|
| DE | 1391324 | 5/1972 |
| DE | 2238457 | 2/1974 |
| DE | 2353639 | 8/1975 |
| EP | 1 391 324 | 4/1975 |
| FR | 1562142 | 2/1969 |
| JP | 60-221403 | 11/1985 |

OTHER PUBLICATIONS

Dorwald F. A. Side Reactions in Organic Synthesis, 2005, Wiley: VCH, Weinheim p. IX of Preface. also p. 8 and 9.*

* cited by examiner

*Primary Examiner*—Rita J Desai
(74) *Attorney, Agent, or Firm*—Dorsey & Whitney LLP

(57) ABSTRACT

The invention discloses novel sulfur-containing naphthalimide derivatives, and the preparation and uses thereof. The conjugated plane of naphthalimide derivatives of the invention is enlarged by incorporating 5-or 6-membered heteroaromatic ring and/or introducing S heteroatom, thus increasing the anti-tumor activity of naphthalimide. The compounds of the invention displays significant inhibiting activities to the proliferation of various tumor cells such as human lung cancer, gastric cancer, liver cancer, leucocythemia and the like. The inhibition of cell proliferation is dose-dependent.

4 Claims, No Drawings

SULFUR-CONTAINING NAPHTHALIMIDE DERIVATIVES

CROSS-REFERENCE TO RELATED APPLICATIONS

This application is a continuation of International application number PCT/CN2004/000442, filed Apr. 30, 2004 which claims priority to Chinese application No. CN 03116709.8 filed Apr. 30, 2003, the contents of both are herein incorporated in their entirety by reference.

TECHNICAL FIELD

This invention relates to novel sulfur-containing naphthalimide derivatives having anti-tumor activities, and to the preparation and uses thereof.

BACKGROUND ART

Mononaphthalimide compounds without heterocycle in the aromatic ring are a type of compounds having good anti-tumor activity, of which amonafide (N-(β-dimethylaminoethyl)-3-amino-1,8-naphthalimide) and mitonafide (N-(β-dimethylaminoethyl)-3-nitro-1,8-naphthalimide) have shown the best activity and both entered the Phase II clinical trials (Brana M. F., Santos A., Roldan C. M., et al. Eur. J. Med. Chem. Chim. Ther., 1981, 16, 207). These compounds can insert the base-pair of DNA, inhibit the synthesis of DNA and RNA, and inhibit Topoisomerase II, thus inhibiting tumor.

However, the anti-tumor effect of the compounds is still unsatisfying, so there is an urgent need in the art for developing new compounds with high anti-tumor activity.

SUMMARY OF INVENTION

The object of the present invention is to provide a class of naphthalimide compounds with higher anti-tumor activity.

After intensive and extensive study, it is found for the first time that when S atom is introduced to naphthalimide, especially when heterocycle and S atom are introduced to the aromatic ring, the plane of the aromatic ring is enlarged and/or the rigidity of the aromatic ring plane is enhanced, and the embedding ability of naphthalimide for DNA is increased, thus increasing the anti-tumor activity of naphthalimide. It has been proved in experiments that, sulfur-containing naphthalimide of the present invention displays very strong inhibiting activities on the growth of tumor cell in vitro.

In the first aspect of the present invention, it is provided compounds represented by the formula (I) or pharmaceutically acceptable salts thereof:

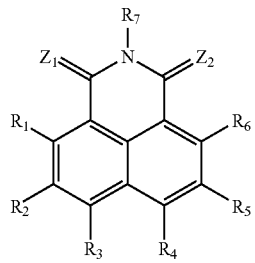

(I)

wherein:

$R_1$, $R_2$, and $R_6$ are independently selected from the group consisting of: H, $C_1$-$C_6$ alkyl, $C_1$-$C_6$ haloalkyl, $C_1$-$C_3$ alkoxy, halogen, hydroxy, amino, and —CN;

$R_3$, $R_4$, and $R_5$ independently represent H, $C_1$-$C_6$ alkyl, $C_1$-$C_6$ haloalkyl, $C_1$-$C_3$ alkoxy, halogen, hydroxy, amino, or —CN; or, $R_3$ and $R_4$ or $R_4$ and $R_5$ together form a 5-6 membered heterocyclic ring or an aryl-fused 5-6 membered heterocyclic ring;

The heterocyclic ring has 1-3 hetero-atoms selected from S, N, and O, and is optionally substituted with 1-3 substituents selected from the group consisting of: aryl, heteroaryl, $C_1$-$C_6$ alkyl, $C_1$-$C_6$ haloalkyl, $C_1$-$C_6$ alkoxy, $C_1$-$C_6$ haloalkoxy, halogen, —$NH_2$, $C_1$-$C_3$ amino substituted with alkyl, —$NO_2$, —OH, —CN, acyl group containing 1-3 carbon atoms, and sulfonic group;

The aryl and heteroaryl group is optionally substituted with 1-3 substituents selected from the group consisting of: $C_1$-$C_6$ alkyl, $C_1$-$C_6$ haloalkyl, $C_1$-$C_6$ alkoxy, $C_1$-$C_6$ haloalkoxy, halogen, —$NH_2$, —$NO_2$, —OH, —CN, acyl group containing 1-3 carbon atoms, and sulfonic group;

$Z_1$ and $Z_2$ are O or S;

with the proviso that at least one of $Z_1$ and $Z_2$ is S when $R_3$, $R_4$ and $R_5$ do not contain S, $R_7$ represents $C_1$-$C_6$ alkyl, $C_2$-$C_8$ alkenyl, -($C_1$-$C_6$ alkyl)-$NH_2$, -($C_1$-$C_6$ alkyl) N ($C_1$-$C_4$ alkyl)$_2$, -($C_1$-$C_6$ alkyl) piperazine, arylacyloxy, heterocyclic acyloxy group; wherein the heterocyclic ring has 1-3 hetero-atoms selected from S, N, and O and is optionally substituted with 1-3 substituents selected from the group consisting of: $C_1$-$C_6$ alkyl, $C_1$-$C_6$ haloalkyl, $C_1$-$C_6$ alkoxy, $C_1$-$C_6$ haloalkoxy, halogen, —$NH_2$, —$NO_2$, —OH, —CN;

And the heterocyclic ring is optionally substituted with 1-3 substituents selected from the group consisting of: $C_1$-$C_6$ alkyl, $C_1$-$C_6$ haloalkyl, $C_1$-$C_6$ alkoxy, $C_1$-$C_6$ haloalkoxy, halogen, —$NH_2$, —$NO_2$, —OH, —CN and sulfonic group;

with the proviso that $R_7$ is not $CH_2CH_2N (CH_3)_2$ when $R_4$ and $R_5$ form thienyl group; and that the compound is not N-butyl benzo[k, l]thioxanthene-3,4-dicarboximide (compound 1) or N-(N', N'-dimethylaminopropyl)benzo[k, l]thioxanthene-3,4-dicarboximide (compound 4).

Preferably, the compound has the following formula:

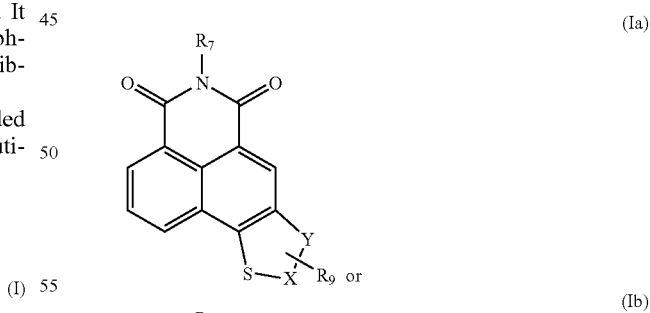

(Ia)

or

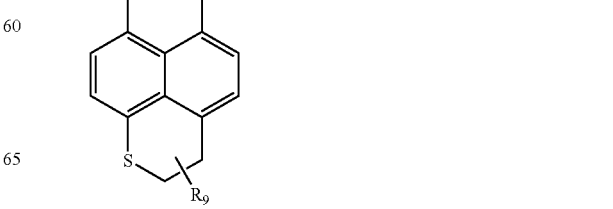

(Ib)

wherein:

R₉ is absent, aromatic ring, substituted aromatic ring, heteroaromatic ring, or substituted heteroaromatic ring, wherein the ring may contain 1-3 substituents selected from the group consisting of: $C_1$-$C_6$ alkyl, $C_1$-$C_6$ haloalkyl, $C_1$-$C_6$ alkoxy, $C_1$-$C_6$ haloalkoxy, halogen, —NH₂, $C_1$-$C_3$ amino substituted with alkyl, —NO₂, —OH, —CN, acyl group containing 1-3 carbon atoms, and sulfonic group;

X and Y are C or N;

with the proviso that R₉ is absent when X=Y=N.

In another preferred embodiment, the aryl group is phenyl with 0-3 substituents.

In another preferred embodiment, the heterocyclic ring has at least one S atom.

In another preferred embodiment, the compound is attached to S in positions 3 or 4.

In another preferred embodiment, R₃ and R₄ or R₄ and R₅ form the following groups:

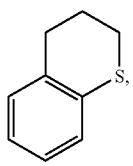

thiazolyl, benzthiazolyl, thiodiazole, thiophene, benzthiophene, wherein the groups is optionally substituted with 1-3 substituents selected from the group consisting of: $C_1$-$C_6$ alkyl, $C_1$-$C_6$ alkoxy, halogen, —NO₂, —OH, —NH₂, phenyl and benzyl group.

In another preferred embodiment, R₇ is: —CH₂CH₂CH₂CH₃, —CH₂CH₂N (CH₃)₂,

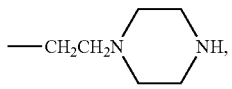

—CH₂CH₂CH₂N (CH₃)₂, —CH₂CH (OOH)C (=CH₂)CH₃, —CH₂CH (OH)C (=CH₂)CH₃, —CH₂CH=CH (CH₃)₂, —CH₂CH₂CH (OOH)C (=CH₂)CH₃, —CH₂CH₂CH=CH (CH₃)₂, substituted or unsubstituted benzoyloxy, or substituted or unsubstituted furyl acyloxy (furyl-COO—), wherein the substituents are 1-3 groups selected from the group consisting of: $C_1$-$C_6$ alkyl, $C_1$-$C_6$ alkoxy, halogen, and —OH.

More preferably, the compounds are compound 2, 3, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 showed in Table 1.

In the second aspect of the present invention, it is provided a pharmaceutical composition comprising compounds of formula (I) or their pharmaceutically acceptable salts of the present invention and pharmaceutically acceptable carriers or excipients. It is also provided the use of compounds of formula (I) or pharmaceutically acceptable salts thereof in the preparation of medicine. The preferable compounds of formula (I) include compounds 1-34 showed in Table 1.

MODE OF CARRYING OUT THE INVENTION

The term "alkyl" used herein refers to straight and branched chain, saturated aliphatic group containing 1-8 (preferably 1-6) carbon atoms; "alkenyl" includes straight and branched chain hydrocarbon group containing at least one double bond between two carbon atoms and 2-8 carbon atoms; "alkynyl" includes straight and branched chain hydrocarbon group containing at least one triple bond between two carbon atoms and 2-8 carbon atoms.

The terms "substituted alkyl", "substituted alkenyl" and "substituted alkynyl" refer to the above-described alkyl, alkenyl, or alkynyl groups substituted with one or more substituents selected from the group consisting of: halogen, CN, OH, NO₂, amino, aryl, heterocyclic, substituted aryl, substituted heterocyclic, alkoxy, aryloxy, substituted alkoxy, alkylcarbonyl, alkylcarboxyl, alkylamino, thioaryl. These substituents may attach to any carbon atom of alkyl, alkenyl or alkynyl, with the proviso that this attachment forms stable chemical structure.

The term "aryl" used herein refers to aromatic system and may be monocyclic or polycyclic aryl group fused together or attached together, thus making at least a portion of fused or attached rings forming conjugated aromatic system. Representative aryl groups include (but not limited to): phenyl, naphthenyl, biphenyl, anthracenyl, tetrahydronaphthenyl, phenanthryl.

The term "substituted aryl" refers to the above-described aryl groups substituted with 1-3 substituents selected from the group consisting of: halogen, CN, OH, NO₂, amino, aryl, cycloalkyl, alkenyl, alkynyl, alkoxy, aryloxy, substituted alkoxy, alkylcarbonyl, alkylcarboxyl, alkylamino or thioaryl group.

The term "heterocyclic" used herein refers to stable 4-7membered (preferably 5-6) monocyclic or stable polycyclic heterocyclic rings. The heterocyclic ring may be saturated, partially unsaturated or unsaturated, and it consists of carbon atoms and 1-3 hetero-atoms selected from N, O and S atoms. N and S atom may be oxidized. The heterocyclic ring may include any polycyclic ring, wherein any of the polycyclic rings can be fused to the aromatic ring. The heterocyclic ring may attach to any heteroatom or carbon atom, with the proviso that the forming structure must be chemically stable. The heterocyclic rings include (but not limited to):

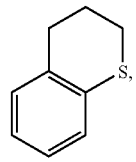

thiazole, benzothiazolyl, thiadiazole, thiophene, benzothiophene, tetrahydrofuran, piperidyl, piperazinyl, 2-oxo piperidyl, pyrrolidinyl, imidazolyl, pyridinyl, pyrazinyl, pyrimidinyl, pyridazinyl, oxazolyl, isooxazolyl, morpholinyl, indolyl, quinolyl, furyl, benzofuryl, thiomorpholiny, thiomorpholinysulfoxide and isoquinolyl.

The term "substituted heterocyclic" used herein refers to the above-described heterocyclic groups substituted with 1-3 substituents selected from the group consisting of: aryl, halogen, CN, OH, NO₂, amino, alkyl, substituted alkyl, cycloalkyl, alkenyl, substituted alkenyl, alkynyl, alkoxy, aryloxy, substituted alkoxy, or thioaryl group. The term "alkoxy" refers to OR group, wherein R is alkyl or substituted alkyl. The term "aryloxy" refers to OR group, wherein R is aryl or substituted aryl. The term "halogen" refers to Cl, Br, F and I.

The compounds of the present invention can be prepared from the material 4-bromo-3-nitro-1, 8-naphthalic anhydride, by substitution, reduction and cyclization to form the parent anhydride, which then reacts with amine to form the target compound.

For example, the starting material 4-bromo-1,8-naphthalic anhydride reacts with ortho-amino thiophenol to form 4-(2-aminothiophenyl)-1,8-naphthalic anhydride. Then the key intermediate benzo[k,l]thioxanthene-3,4-dicarboxanhydride which reacts with various amines to form the desired target compound 1-4 is obtained after the diazotization-Pschorr cyclization. Starting from 4-bromo-1,8-naphthalic anhydride, sodium polysulfide is used to reduce nitro group and replace bromine in position 4 after nitration. Then under argon atmosphere, the reduction liquid is added to the mixture of aromatic aldehyde and acetic acid dropwise, and the resultant free 4-mercapto-3-amino-1,8-naphthalic anhydride is cyclized with aldehyde under inert atmosphere to yield the key intermediate 2-(substituted)phenyl thiadiazolnaphthalic anhydride, which is finally condensed with amines to yield target compounds 5-10. Starting from 4-bromo-1, 8-naphthalic anhydride, 4-bromo-3-nitro-1,8-naphthalic anhydride is obtained after sulfuric acid/sodium nitrate nitration. Then, benzyl sulfhydrate is employed to replace the bromine in position 4 to yield 4-benzylsulfhydryl-3-nitro-1,8 naphthalic anhydride. After tin dichloride/hydrochloric acid reduction, 4-benzylsulfhydryl-3-amino-1,8 naphthalic anhydride is obtained. Finally, diazotization cyclization gives the key intermediate thiadiazolnaphthalic anhydride, which is reacted with various amines to yield the target compounds 11-14. Starting from 4-bromo-1,8-naphthalic anhydride, 4-bromo-3-nitro-1,8-naphthalic anhydride is obtained after nitration. Then, it is reacted with thiophenol to yield 4-thiophenyl-3-nitro-1,8-naphthalic anhydride. Then 4-thiophenyl-3-amino-1, 8-naphthalimide is obtained by tin dichloride/hydrochloric acid reduction. Finally, the key intermediate benzothienonaphthalic anhydride is obtained after diazotization-Pschorr cyclization. It reacts with various amines to yield the target compounds 15-18. The other compounds of the present invention can be prepared using similar methods.

The compounds of the present invention can be used in the form of pharmaceutically or physiologically acceptable salts derived from acids or bases, eaters, carbamyl esters or other conventional "prodrugs" (They can be converted into the active ingredient in body when administered in this form). The salts include (but not limited to) those formed with the following aids: such as hydrochloric acid, sulfuric acid, nitric acid, phosphoric acid; and the salts formed with organic acids, wherein organic acids refer to acetic acid, oxalic acid, butyl dicarboxylic acid and maleic acid. Other salts include those formed with alkali metals or alkaline-earth metals (such as sodium, potassium, calcium or magnesium).

It is also provided a pharmaceutical composition and a treating method comprising administering a pharmaceutically effective amount of one or more of the above compounds as tumor-treating agent to the mammal animals.

Single or combination of the tumor-treating agents of the present invention can be used to treat and/or prevent benign and malignant tumors. The compounds and pharmaceutical composition of the present invention can be used to treat lung cancer, gastric cancer, liver cancer, leucocythemia, endometrioma, oophoroma, mammary cancer, colon cancer, prostatic cancer, pituitary gland cancer and the like.

When the compounds are used for the above purposes, they may be mixed with one or more pharmaceutical acceptable carrier or excipient, such as solvent, diluent and the like. They can be orally administered in the following forms: tablets, capsules, dispersible powders, granules or suspensions (containing such as about 0.05-5% suspending agents), syrups (containing such as about 10-50% sugar), and elixirs (containing about 20-50% ethanol), or they can be parenterally administered in the form of a sterile injection or suspension (isotonic medium contains about 0.05-5% suspending agents). For example, these pharmaceutical preparations may contain about 25-90%, generally about 5%-60% active ingredient by weight mixed with the carriers.

The effective amount of the used active ingredient depends on the specific compound employed, mode of administration and the severity of the disease. However, when the daily dose of the compounds of this invention is administered to animals in amounts from 0.5 to 500 mg/kg body weight, the effect is generally satisfying. Preferably, 1-4 dosages may be administered daily, and the dosage may be administered in slow-released forms. For most large mammals, daily total dosage is about 1-100 mg, preferred about 2-80 mg. Dosage forms suitable for oral administration include 0.5-500 mg active compound mixed with pharmaceutically acceptable solid or liquid carriers. The dosage scheme may be adjusted to provide the best therapeutic response. For example, according to the therapeutic conditions, the dosage may be divided to several parts, or the dosage may be reduced proportionally.

These active compounds may be administered orally, intravenously, intramuscularly or subcutaneously. Solid carrier includes: starch, lactose, calcium dihydrogenphosphate, microcrystalline cellulose, sucrose and kaolin, while liquid carrier includes: sterile water, polyethylene glycol, non-ionic surfactant and edible oil (such as corn oil, peanut oil and sesame oil), as long as they are suitable for the specialty of the active ingredient and the specific desired administration mode. Adjuvants, such as flavoring agent, pigment, preservative and antioxidant, such as vitamin E, vitamin C, BHT and BHA may be advantageously included in the preparation of pharmaceutically composition.

From the standpoint of preparation and administration, preferable pharmaceutically composition is solid composition, in particular, tablets or capsules filled with solid or liquid. Oral administration of compounds is preferred.

These active compounds may be parenterally administered. The solution or suspension of the active compounds (as free bases or pharmaceutically acceptable salts) can be prepared in water properly mixed with surfactant (such as hydroxymethyl cellulose). The dispersing solution can be prepared in glycerol, liquid, polyethylene glycol and the mixture of polyethylene glycol in oil. Under conventional storage and use conditions, preservatives are included in the preparations to prevent the growth of microorganism.

Medicine forms suitable for injection include: sterile aqueous solution or dispersing solution and sterile powders (used for temporarily preparing sterile injection or dispersing solution). In all cases, these forms must be sterile and must be fluid in order to make it easy for the injector to discharge the fluid. They must be stable in the conditions of preparation and storage, and they must prevent microorganism (such as bacteria and fungi) from polluting them. Carriers may be solvents or dispersing mediums, including, e.g., water, alcohol (such as glycerol, propylene glycol and polyethylene glycol), mixtures thereof and vegetable oil.

Compared with the existing compounds, the main advantages of the compounds of the invention are as follows: due to the introduction of S atom and/or merging of heterocycle to the aromatic ring, the embedding ability of naphthalimide into DNA is increased, thus the anti-tumor activity of naphthalimide is increased. Experiments have showed that the compounds of the present invention display a wide-ranging anti-tumor activity, especially the significant inhibiting activities to the proliferation of various tumor cells, such as human lung cancer, gastric cancer, liver cancer, leucocythemia and the like. The inhibition of cell proliferation is dose-dependent.

The invention is further illustrated by the following examples. It is appreciated that these examples are only intended to illustrate the invention, but not to limit the scope of the invention. For the experimental methods in the following examples, they are performed under routine conditions, or as instructed by the manufacturers, unless otherwise specified.

EXAMPLE 1

Preparation of N-(N',N'-dimethylaminoethyl)benzo[k, l]thioxanthene-3,4-dicarboximide (compound 2)

A reaction mixture containing 0.3 g of benzo[k, l]thioxanthene-3,4-dicarbox-imide (Tetrahedron.2002, 43, 2995-2998), 20 ml of anhydrous ethanol, 0.162 ml of N, N-dimethylethylenediamine in 50 ml of round bottom flask was refluxed with stirring for 2 hours until there was no raw material (TCL monitored). After cooling, the solvent was removed and the residue was purified using column chromatography, chloroform-acetone (1:1) eluted the title compound (0.314 g, 85%), mp 212-213° C. (uncorrected). $^1$H NMR (CDCl$_3$) δ (ppm): 1.27 (m, 8H), 4.42 (t, $J_1$=6.78 Hz, $J_2$=6.65 Hz, 2H), 7.39 (m, 3H), 7.48 (d, J=7.99, 1H), 8.18 (m, 2H), 8.40 (d, J=7.98 Hz, 1H), 8.59 (d, J=8.12, 1H). IR (KBr): 2950, 2870, 1695, 1660, 1560, 1380 cm$^{-1}$. MS: m/z (%)374 (M$^+$) (1.62), 304 (23.30), 303 (29.64), 71 (29.58), 58 (100), 56 (9.81), 43 (12.49). Anal. (%) calcd for $C_{22}H_{18}N_2O_2S$: C, 70.57, H 4.85; N 7.48, S 8.56. found: C, 70.46, H 4.98; N 7.35, S 8.83.

EXAMPLE 2

Preparation of N-(2'-piperazinylethyl)benzo[k, l]thioxanthene-3,4-dicarboximide (compound 3)

Following the procedure described in Example 1 but using in place of N, N-dimethylethylenediamine a molar equivalent quantity of the appropriate 1-(2-aminoethyl)piperazine, the title compound was obtained, mp 286-287° C. (uncorrected). $^1$H NMR (d$_6$-DMSO) δ (ppm): 2.80 (t, J1=5.96, J2=6.00, 2H), 2.89 (s, 4H), 3.14 (s, 4H), 4.32 (t, J1=6.08, J2=5.88, 2H), 7.41 (m, 3H), 7.54 (d, J=8.06, 1H), 8.24 (m, 2H), 8.42 (d, J=8.01, 1H), 8.62 (d, J=8.18, 1H). IR (KBr): 3410, 2970, 2840, 1690, 1640, 1330 cm$^{-1}$. MS: m/z (%) 415 (M$^+$) (5.45), 373 (39.42), 330 (35.98), 303 (27.95), 99 (100.0), 70 (27.95), 56 (42.09), 42 (21.07). Anal. (%) calcd for $C_{24}H_{21}N_3O_2S$: C, 69.38, H 5.09; N 10.11. found: C, 69.56; H, 5.23, N, 9.96.

EXAMPLE 3

Preparation of N-(N',N'-dimethylaminoethyl)-4H, 6H-9-m-nitrophenyl-benzo[de]thiazol[5,4-g]isoquinoline4,6-diketone (compound 7)

(1) A reaction mixture containing Na$_2$S.9H$_2$O (0.009 mol) and sulfur (0.018 mol) in water was heated below 40° C. until sulfur was completely dissolved, 4-bromine-3-nitro-1,8-naphthalic anhydride (0.0025 mol) (4) (J. Soc. Dyers Colourists 1974, 90, 153) was added. After stirred at reflux for 8 h, the solution was allowed to cool at ambient temperature and then in an ice-water bath for another 30 min. After filtration, wine filtrate was obtained. m-nitrobenzaldehyde (0.00275 mol) was added to glacial acetic acid under argon atmosphere at 50° C. for 30 min, and the wine filtrate above was added dropwise. The reaction mixture was refluxed for 4 h. The mixture was allowed to cool to ambient temperature and stirred for another 4 h. Then the mixture was poured into ice-water. The mixture was filtered and the precipitate was collected. The precipitate was dissolved in NaOH aqueous solution. After filtration, the filtrate was acidified with hydrochloric acid. A solid precipitated, which was filtered, washed with water and dried in vacuo to give a solid (0.520 g, 55%).

(2) To a solution of the solid prepared above (0.52 g) in anhydrous ethanol was added N, N-dimethylethylenediamine (0.239 ml). The mixture was refluxed until the reaction was completed (TCL monitored). The precipitate was filtered off and purified using column chromatography to give the title compound (0.17 g, 28%): mp 229-230° C. (uncorrected).$^1$H-NMR (d$_6$-DMSO)δ (ppm): 2.27 (s, 6H), 2.59 (s, 2H), 4.21 (s, 2H), 7.91 (d, 1H, J=5.55), 8.00 (m, 1H), 8.44 (m, 1H), 8.53 (m, 2H), 8.62 (m, 1H), 8.80 (m, 1H), 8.89 (m, 1H). IR (KBr): 2970, 2800, 2750, 1700, 1660, 1525, 1340, 780 cm$^{-1}$. EI-MS; m/z (%)446.0 (M$^+$) (1.47), 388.0 (1.05), 358.0 (1.79), 342 (1.10), 258.0 (1.62), 157.0 (1.98), 71.1 (41.03), 58.1 (100).

Anal. (%) calcd for $C_{23}H_{18}N_4O_4S$: C, 61.87; H, 4.06; N, 12.55. found: C, 62.03; H, 4.31; N, 12.79.

EXAMPLE 4

Preparation of N-(N',N'-dimethylaminoethyl)-4H, 6H-9-phenyl-benzo[de]thiazol[5,4-g]isoquinoline-4, 6-diketone (compound 5)

Following the procedure described in Example 1 but using in place of m-nitrobenzaldehyde a molar equivalent quantity of the appropriate benzal-dehyde, the title compound was obtained, mp 220-221° C. (uncorrected). $^1$H-NMR (d$_6$-DMSO) δ (ppm): 2.25 (s, 8H), 4.20 (s, 2H), 7.66 (d, J=4.54 Hz, 3H), 8.03 (t, $J_1$=7.79, $J_2$=7.57, 1H), 8.21 (m, 2H), 8.56 (d, J=6.97, 1H), 8.67 (d, J=7.49, 1H), 8.95 (s, 1H).IR (KBr): 2960, 2800, 1700, 1660, 1320, 780 cm$^{-1}$. HR-MS; calcd for $C_{23}H_{19}N_3O_2S$: 401.1198; found: 401.1186; EI-MS m/z (%) 401 (M$^+$) (5.46), 343 (5.73), 313 (8.58), 285 (9.97), 157 (7.56), 71 (41.4), 58 (100).

Anal. (%) calcd for $C_{23}H_{19}N_3O_2S$: C, 68.81; H, 4.77; N 10.47. found: C, 68.54; H, 4.89, N, 10.51.

EXAMPLE 5

Preparation of N-(N',N'-dimethylaminoethyl)-4H, 6H-9-p-methylphenyl-benzo[d, e]thiazol[5,4-g]isoquinoline4,6-diketone (compound 6)

Following the procedure described in Example 1 but using in place of m-nitro benzaldehyde a molar equivalent quantity of the appropriate p-methylbenzaldehyde, the title compound was obtained, mp 202-203° C. (uncorrected).

$^1$H-NMR (d$_6$-DMSO)δ (ppm): 2.31 (s, 6H), 2.43 (s, 5H), 4.22 (s, 2H), 7.46 (d, J=7.91 Hz, 2H), 8.03 (t, $J_1$=7.81, $J_2$=7.83, 1H), 8.10 (d, J=7.85 Hz, 2H), 8.57 (d, J=7.19, 1H), 8.66 (d, J=8.11, 1H), 8.94 (s, 1H).IR (KBr): 2960, 2820, 1700, 1660, 1325, 790 cm$^{-1}$. EI-MS: m/z (%)415.1 (M$^+$) (15.48), 371 (3.51), 327 (5.66), 299 (6.45), 157 (6.50), 71

(71.0), 58 (100). Anal. (%) calcd for $C_{24}H_{21}N_3O_2S$: C, 69.38; H, 5.09; N 10.11. found: C, 69.30; H, 4.71, N, 10.25.

EXAMPLE 6

Preparation of N-(N',N'-dimethylaminoethyl)-4H, 6H-9-p-methoxy phenyl-benzo[de]thiazol[5,4-g] isoquinoline-4,6-diketone (compound 9)

Following the procedure described in Example 1 but using in place of m-nitrobenzaldehyde a molar equivalent quantity of the appropriate p-methoxy benzaldehyde, the title compound was obtained, mp 216-217° C. (uncorrected).

$^1$H-NMR ($d_6$-DMSO) δ (ppm): 2.27 (s, 6H), 2.61 (s, 2H), 3.89 (s, 3H), 4.21 (t, 2H, $J_1$=6.56, $J_2$=6.64), 7.19 (d, J=8.66 Hz, 2H), 8.01 (t, $J_1$=7.77, $J_2$=7.77, 1H), 8.15 (d, J=8.50 Hz, 2H), 8.55 (d, J=7.28, 1H), 8.63 (d, J=8.18, 1H), 8.91 (s, 1H).IR (KBr): 2970, 2810, 1700, 1665, 1330, 780 $cm^{-1}$. HR-MS; calcd for $C_{24}H_{21}N_3O_3S$: 431.1304. found 431.1311; EI-MS m/z (%)431.1311 ($M^+$) (3.39), 386.0719 (2.49), 343.0533 (1.70), 246.0349 (1.69), 157.0111 (1.75), 71.0732 (73.67), 58:0622 (100).

Anal. (%) calcd for $C_{24}H_{21}N_3O_3S$: C, 66.80; H, 4.91; N 9.74. found: C, 66.94; H, 4.73, N, 10.03.

EXAMPLE 7

Preparation of N-(N',N'-dimethylaminoethyl)-4H, 6H-9-o-chlorophenyl-benzo[de]thiazol[5,4-g]isoquinoline-4,6-diketone (compound 10)

Following the procedure described in Example 1 but using in place of m-nitrobenzaldehyde a molar equivalent quantity of the appropriate o-chloro benzaldehyde, the title compound was obtained, mp 235-237° C. (uncorrected).

$^1$H-NMR ($d_6$-DMSO)δ (ppm): 2.28 (s, 6H), 2.62 (d, 2H, J=1.44), 4.19 (t, 2H, $J_1$=6.78, $J_2$=6.81), 7.63 (m, 2H), 7.76 (m, 1H), 7.99 (t, $J_1$=7.74, $J_2$=7.75, 1H), 8.38 (dd, $J_1$=1.78, $J_2$=7.50, 1H), 8.54 (d, J=7.32, 1H), 8.70 (d, J=8.17, 1H), 8.94 (s, 1H).IR (KBr): 2980, 2800, 1700, 1660, 1340, 780 $cm^{-1}$.

HR-MS; calcd for $C_{23}H_{18}ClN_3O_2S$: 435.0808. found 435.0792;

EI-MS: m/z (%)435.0792 ($M^+$) (5.06), 377.0117 (2.45), 347.0052 (4.14), 319.0059 (4.03), 259.0427 (1.14), 157.0104 (7.16), 71.0733 (67.76), 58.0610 (100).

Anal. (%) calcd for $C_{23}H_{18}ClN_3O_2S$: C, 63.37; H, 4.16; N 9.64. found: C, 63.42; H, 4.43, N, 9.35.

EXAMPLE 8

Preparation of N-(N',N'-dimethylaminoethyl)-4H, 6H-9-o-hydroxyphenyl-benzo[de]thiazol[5,4-g]isoquinoline-4,6-diketone (compound 8)

Following the procedure described in Example 1 but using in place of m-nitrobenzaldehyde a molar equivalent quantity of the appropriate o-hydroxy benzaldehyde, the title compound was obtained, mp 240-241° C. (uncorrected).

$^1$H-NMR ($d_6$-DMSO)δ (ppm): 2.27 (s, 6H), 2.60 (s, 2H), 4.21 (t, 2H, $J_1$=6.88, $J_2$=6.95,), 7.07 (t, 1H, $J_1$=7.39, $J_2$=7.32), 7.15 (d, 1H, J=8.21), 7.47 (m, 1H), 7.99 (t, $J_1$=7.76, $J_2$=7.81, 1H), 8.30 (dd, $J_1$=1.46, $J_2$=8.11, 1H), 8.53 (d, J=7.25, 1H), 8.71 (d, J=8.10, 1H), 8.94 (s, 1H).IR (KBr): 2980, 2800, 2500 (Br), 1700, 1660, 1330, 780 $cm^{-1}$. HR-MS; calcd for $C_{23}H_{19}N_3O_3S$: 417.1147. found 417.0342; EI-MS:m/z (%)417.0342 ($M^+$) (6.20), 372.9947 (2.65), 358.9714 (3.38), 300.9830 (4.03), 259.0427 (4.62), 156.9798 (8.19), 71.0554 (100), 58.0452 (88.55).

Anal. (%) calcd for $C_{23}H_{19}N_3O_3S$: C, 66.17; H, 4.59, N, 10.07. found, C, 66.34; H, 4.78, N, 9.89.

EXAMPLE 9

Preparation of 5-(N',N'-dimethylaminoethyl)-4H, 6H-benzo[de]-1, 2, 3,-thiadiazol[5, 4-g]isoquinoline-4, 6-diketone (compound 8)

(1) 4-benzylsulhydryl-3-nitro-1,8-naphthalic anhydride 4-bromo-3-nitro-1,8-naphthalic anhydride (0.0072 mol) (4) was dissolved in DMF (45 ml) in 100 ml of three-neck flask. After addition of $K_2CO_3$ (0.0036 mol) and benzyl sulfhydrate (0.0072 mol), the solution was stirred at 80° C. for 8 h until there was no raw material. The reaction mixture was poured into ice-water, then salted out under stirring. A yellow solid precipitated after filtration and washing by water and dried to give khaki solid (2.47 g, 83%): mp 188-193° C. (uncorrected).

(2) 4-benzylsulhydryl-3-amino-1,8-naphthalic anhydride

A reaction mixture containing 0.0068 mol of 4-benzylsulhydryl-3-nitro-1, 8-naphthalic anhydride, 7.6 g of $SnCl_2.2H_2O$ and 31 ml concentrated hydrochloric acid in 100 ml of three-neck flask was stirred at 90° C. for 2 h until there was no raw material (TCL monitored), excessively 10-20 ml of concentrated hydrochloric acid was added during the reaction. The reaction mixture was poured into ice-water. After filtration and dried, a yellow solid was obtained which possibly contain $SnCl_4$ (2.85 g, 126%), mp 171-185° C.

(3) 1, 2, 3-thiadiazol-1,8-naphthalic anhydride

A reaction mixture containing 0.0044 mol of 4-benzylsulhydryl-3-amino-1, 8-naphthalic anhydride, 57 ml of glacial acetic acid, 7 ml of $H_2O$, 8.5 ml of concentrated hydrochloric acid was stirred at ambient temperature for 30 min to give olivine solution. The solution was allowed to cool in glacial salt bath at −10° C., 10 ml of aqueous sodium nitrite solution was added dropwise to the solution which was then vigorously stirred for 30 min at the same temperature to give red solution. The red solution was stirred in ice-water bath for 3.5 h and another 3.5 h in water bath where the temperature was keeping at 15-20° C. until there was no raw material (TCL monitored). After filtration, the precipitate was washed by 1% aqueous sodium bicarbonate solution until neutrality and dried in vacuo to give olivine solid (0.97 g, 86%).

(4) 5-(N',N'-dimethylaminoethyl)-4H, 6H-benzo[de]-1,2,3,-thiadiazol[5,4-g]isoquinoline-4,6-diketone A reaction mixture containing 0.28 g of 1, 2, 3-thiadiazol-1,8-naphthalic anhydride, anhydrous ethanol (20 ml) and N, N-dimethylethylenediamine (0.189 ml) in 50 ml of round bottom flask was stirred at reflux for 2 h until there was no raw material (TCL monitored). After cooling, the solvent was removed and the residue was purified using column chromatography to give flavescent title compound (0.25 g, 70%), mp 178-179° C.

¹H NMR (d₆-DMSO) δ (ppm): 2.25 (s, 6H), 2.57 (t, $J_1$=6.87 Hz, $J_2$=6.97 Hz, 2H), 4.19 (t, $J_1$=6.86 Hz, $J_2$=6.99 Hz, 2H), 8.06 (t, $J_1$=8.06 Hz, $J_2$=7.72 Hz, 1H), 8.64 (d, J=7.44 Hz, 1H), 8.85 (d, J=8.04 Hz, 1H), 9.38 (d, J=1.52 Hz, 1H).IR (KBr): 2940, 2870, 1700, 1660, 1300 cm⁻¹ HR-MS: calcd for $C_{16}H_{14}N_4O_2S$: 326.0837, found 326.0788. EI-MS: m/z (%)326.0788 (M⁺) (25.29), 254.0261 (14.92), 209.9968 (39.54), 182.0024 (45.43), 155.9992 (42.73), 71.0683 (84.29), 58.0493 (82.70). Anal. (%) calcd for $C_{16}H_{14}N_4O_2S$: C, 58.88; H, 4.32, N, 17.17. found: C, 58.69; H, 4.17, N, 17.05.

EXAMPLE 10

Preparation of 5-(N',N'-dimethylaminopropyl)-4H, 6H-benzo[de]-1,2,3,-thiadiazol[5,4-g]isoquinoline-4,6-diketone (compound 13)

Following the procedure described in Example 7 but using in place of N, N-dimethylethylenediamine a molar equivalent quantity of the appropriate N, N-dimethylpropylenediamine, the title compound was obtained, mp 101-102° C. (uncorrected).

¹H NMR (CDCl₃) δ (ppm): 1.9 (m, 2H), 2.22 (s, 6H), 2.43 (t, $J_1$=7.16, $J_2$=7.27, 2H), 4.23 (t, $J_1$=7.49, $J_2$=7.66, 2H), 7.91 (t, $J_1$=7.74, $J_2$=7.75, 1H), 8.4 (t, $J_1$=7.86, $J_2$=0.86, 1H), 8.73 (t, $J_1$=7.16, $J_2$=0.81, 1H), 9.58 (s, 1H).IR (KBr): 2960, 2870, 1710, 1670, 1300 cm⁻¹. HR-MS (m/z, %) calcd for $C_{17}H_{16}N_4O_2S$: 340.0994. found 340.0991.MS: m/z (%): 340.0991 (M⁺) (10.41), 240.0145 (2.96), 210.0064 (10.85), 157.0130 (5.39), 84.0832 (71.88), 58.0655 (100). Anal. (%) calcd for $C_{17}H_{16}N_4O_2S$: C, 59.98; H, 4.74, N, 16.46. found: C, 59.74; H, 4.48, N, 16.65.

EXAMPLE 11

Preparation of 5-butyl-4H, 6H-benzo[de]-1,2,3,-thiadiazol[5,4-g]isoquinoline4,6-diketone (compound 12)

Following the procedure described in Example 7 but using in place of N, N-dimethylethylenediamine a molar equivalent quantity of the appropriate n-butylamine, the title compound was obtained, mp 177-179° C. (uncorrected).

¹H NMR (d₆-DMSO) δ (ppm): 0.94 (t, $J_1$=7.33, $J_2$=7.39, 3H), 1.38 (m, 2H), 1.64 (m, 2H), 4.05 (t, $J_1$=7.44, $J_2$=7.54, 2H), 8.03 (t, $J_1$=7.78, $J_2$=7.75, 1H), 8.62 (d, J=7.11, 1H), 8.82 (t, $J_1$=0.70, $J_2$=7.97, 1H), 9.32 (s, 1H). IR (KBr): 2950, 2870, 1710, 1660, 1300 cm⁻¹. HR-MS: calcd for $C_{16}H_{13}N_3O_2S$: 311.0728. found 311.0728. EI-MS: m/z (%): 311.0728 (M⁺) (17.00), 283.0705 (100.00), 266.0659 (27.86), 241.0200 (28.75), 227.0069 (89.84), 157.0128 (23.66). Anal. (%) calcd for $C_{16}H_{13}N_3O_2S$: C 61.72, H 4.21; N 13.50. found: C, 61.59; H, 4.41, N, 13.62.

EXAMPLE 12

Preparation of 5-(2'-piperazinylethyl)-4H, 6H-benzo[de]-1,2,3,-thiadiazol[5,4-g]isoquinoline-4,6-diketone (compound 14)

Following the procedure described in Example 7 but using in place of N, N-dimethylethylenediamine a molar equivalent quantity of the appropriate 1-(2-aminoethyl)-piperazine, the title compound was obtained, mp 145-146° C. (uncorrected).

¹H-NMR (CDCl₃) δ (ppm): 2.54 (s, 4H), 2.67 (t, $J_1$=6.95, $J_2$=6.94, 2H), 2.81 (t, $J_1$=4.76, $J_2$=4.79, 4H), 4.34 (t, $J_1$=6.93, $J_2$=7.01, 2H), 7.92 (t, $J_1$=7.8, $J_2$=7.840, 1H), 8.41 (d, J=7.96, 1H), 8.73 (d, J=7.35, 1H), 9.58 (s, 1H).IR (KBr): 3310, 1710, 1670, 1300 cm⁻¹. HR-MS: calcd for $C_{18}H_{17}N_5O_2S$: 367.1103. found 367.1095.MS (m/z, %): 367.1095 (M⁺, 5.33), 325.0751 (6.87), 282.0327 (4.27), 254.0289 (8.85), 182.0091 (4.53), 157.0128 (2.36)99.0940 (100). Anal. (%) calcd for $C_{18}H_{17}N_5O_2S$: C 58.84, H 4.66; N 19.06. found: C, 58.75; H, 4.92, N, 18.86.

EXAMPLE 13

Preparation of N-(N',N'-dimethylaminoethyl)benzo[b]thieno[2,1-c]naphthalimide (compound 16)

A reaction mixture containing 0.1123 g of N-(N',N'-dimethylaminoethyl) benzo[b]thieno [2, 1-c] naphthalic anhydride (TetrahedronLett. 2002, 43, 2995-2998), 20 ml of anhydrous ethanol and 0.05 ml of N, N-dimethylethylenediamine in 50 ml of round bottom flask was refluxed for 2 h until there was no raw material (TCL monitored), and then was allowed to cool. Filtration gave the title compound (0.1257 g, 91%): mp 171-173° C. (uncorrected).

¹H NMR (d₆-DMSO) δ (ppm): 2.3 (s, 6H), 2.6 (m, 2H, ), 4.21 (t, $J_1$=6.55 Hz, $J_2$=6.62 Hz, 2H), 7.65 (m, 2H), 7.96 (t, $J_1$=7.74 Hz, $J_2$=7.82 Hz, 1H), 8.23 (m, 1H), 8.64 (d, J=7.27 Hz, 1H), 8.66 (m, 2H), 9.28 (s, 1H). IR (KBr): 2940, 2870, 1700, 1660, 1330 cm⁻¹ HR-MS: calcd for $C_{22}H_{18}N_2O_2S$: 374.1089. found 374.1081. EI-MS: m/z (%)374.1081 (M⁺) (21.50), 330.0558 (6.48), 260.0351 (4.55), 232.0327 (14.95), 71.0696 (47.90), 58.0623 (100). Anal. (%) calcd for $C_{22}H_{18}N_2O_2S$: C 70.57, H 4.85; N 7.48. found: C, 70.41; H, 4.97, N, 7.68.

EXAMPLE 14

Preparation of N-(N',N'-dimethylaminopropyl)benzo[b]thieno[2,1-c] naphthalimide (compound 18)

Following the procedure described in Example 11 but using in place of N, N-dimethylethylenediamine a molar equivalent quantity of the appropriate N, N-dimethylpropylenediamine, mp 168-170° C. (uncorrected).

¹H NMR (d₆-DMSO) δ (ppm): 1.95 (m, 2H), 2.24 (s, 6H), 2.45 (m, 2H), 4.2 (t, J1=7.38, J2=7.69, 2H), 7.54 (m, 2H), 7.81 (dd, J1=7.86, J2=7.82, 1H), 7.96 (m, 1H), 8.33 (m, 1H), 8.44 (d, J=7.99, 1H), 8.59 (d, J=6.96, 1H), 9.35 (s, 1H).IR (KBr): 2940, 2880, 1700, 1665, 1330 cm⁻¹.HR-MS: calcd for $C_{23}H_{20}N_2O_2S$: 388.1246. found 388.1253.EI-MS: m/z (%)388.1253 (M⁺) (20.62), 330.0517 (7.80), 317.0350 (10.03), 03.0277 (34.29), 277.0735 (50.50), 246.0314 (20.90), 84.0779 (100), 58.0644 (69.84). Anal. (%) calcd for $C_{23}H_{20}N_2O_2S$: C 71.11, H 5.19; N 7.21. found: C, 71.01, H5.45, N, 7.46.

EXAMPLE 15

Preparation of N-(2'-piperazinylethyl)benzo[b]thieno[2,1-c] naphthalimide (compound 17)

Following the procedure described in Example 11 but using in place of N, N-dimethylethylenediamine a molar equivalent quantity of the appropriate 1-(2-aminoethyl)piperazine, the title compound was obtained, mp 226-228° C. (uncorrected).

¹H NMR (d₆-DMSO) δ (ppm): 2.6 (m, 6H), 3.34 (s, 4H), 4.2 (t, J1=6.47, J2=6.51, 2H), 7.65 (m, 2H), 7.96 (t, J1=7.75, J2=7.82, 1H), 8.2 (m, 1H), 8.54 (d, J=7.27, 1H), 8.64 (m, 2H), 9.25 (s, 1H).IR (KBr): 2950, 2820, 1700, 1670, 1330 cm$^{-1}$. HR-MS: calcd for $C_{24}H_{21}N_3O_2S$: 415.1354; found 415.1349.EI-MS: m/z (%)415.1349 (M$^+$) (8.30), 373.1020 (81.83), 30.0602 (44.08), 304.0417 (17.40), 286.0309 (19.16), 259.0407 (16.70), 99.0890 (100.0), 70.0631 (8.10). Anal. (%) calcd for $C_{24}H_{21}N_3O_2S$: C 69.38, H 5.09; N 10.11. found: C, 69.49; H, 5.37, N, 10.32.

EXAMPLE 16

Preparation of N-butylbenzo[b]thieno[2,1-c]naphthalimide (compound 15)

Following the procedure described in Example 11 but using in place of N, N-dimethylethylenediamine a molar equivalent quantity of the appropriate n-butylamine, the title compound was obtained, mp 226-228° C. (uncorrected).

$^1$H NMR (d$_6$-DMSO) δ (ppm): 0.94 (t, J1=7.36, J2=7.36, 3H), 1.43 (m, 2H), 1.71 (m, 2H), 4.18 (t, J1=7.57, J2=7.62, 2H), 7.54 (m, 2H), 7.79 (t, J1=7.78, J2=7.66, 1H), 7.95 (m, 1H), 8.31 (m, 1H), 8.42 (m, 1H), 8.59 (dd, J1=6.43, J2=0.89, 1H)9.22 (s, 1H).IR (KBr): 2990, 2830, 1700, 1650, 1330 cm$^{-1}$. HR-MS: calcd for $C_{22}H_{17}NO_2S$: 359.0980. found 359.0992.MS: m/z (%)359.0992 (M$^+$) (85.25), 342.1040 (45.10), 317.0563 (65.21), 303.0304 (100.0), 286.0356 (18.72), 259.0480 (19.09), 232.0359 (16.20). Anal. (%) calcd for $C_{22}H_{17}NO_2S$: C 73.51, H 4.77; N 3.90. found: C, 73.46; H, 5.01, N3.18.

EXAMPLE 17-34

Preparation of Compound 1, 4 and 19-34

Compound 1, 4 and 19-34 was prepared according to procedure similar to example 1-16 by using different raw material (Table 1).

TABLE 1

The structures and melting points of compound 1-34

| NO. | STRUCTURE FORMULA | R; $Z_1$, $Z_2$ | M.P. (° C.) |
|---|---|---|---|
| 1 | | $R_1, R_2, R_5, R_6$ = H, $R_7$ = —CH$_2$CH$_2$CH$_2$CH$_3$ $R_3 + R_4$ = $Z_1, Z_2$ = O | 185-186 |
| 2 | | $R_1, R_2, R_5, R_6$ = H, $R_7$ = —CH$_2$CH$_2$N(CH$_3$)$_2$ $R_3 + R_4$ = $Z_1, Z_2$ = O | 212-213 |
| 3 | | $R_1, R_2, R_5, R_6$ = H, $R_7$ = —CH$_2$CH$_2$N⏜NH; $R_3 + R_4$ = $Z_1, Z_2$ = O | 286-287 |

TABLE 1-continued

The structures and melting points of compound 1-34

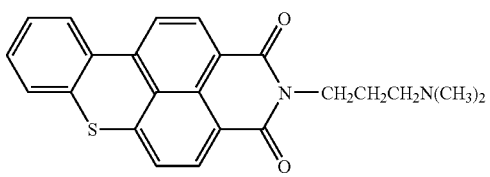

| NO. | STRUCTURE FORMULA | R; $Z_1$, $Z_2$ | M.P. (° C.) |
|---|---|---|---|
| 4 | 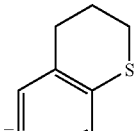 | $R_1, R_2, R_5, R_6 = H$,<br>$R_7 = -CH_2CH_2CH_2N(CH_3)_2$<br><br>$R_3 + R_4 =$ <br><br>$Z_1, Z_2 = O$ | 202-203 |
| 5 | 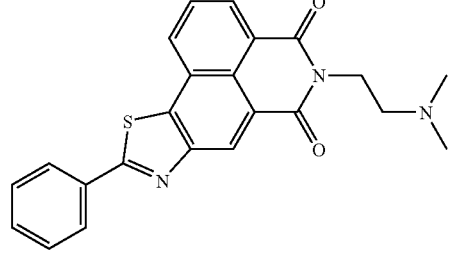 | $R_1, R_2, R_3, R_6 = H$,<br>$R_7 = -CH_2CH_2N(CH_3)_2$<br>$R_4 + R_5 =$ phenyl substituted thiazole<br>$Z_1, Z_2 = O$ | 220-221 |
| 6 | 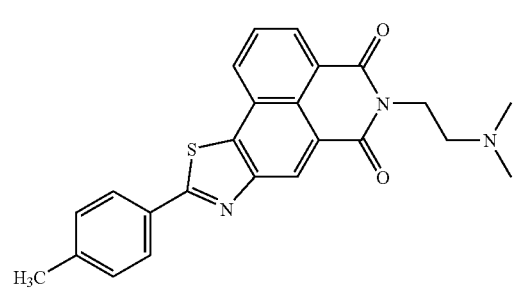 | $R_1, R_2, R_3, R_6 = H$,<br>$R_7 = -CH_2CH_2N(CH_3)_2$<br>$R_4 + R_5 =$ phenyl substituted thiazole<br>$Z_1, Z_2 = O$ | 202-203 |
| 7 | 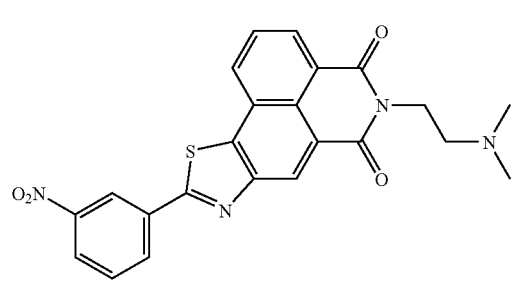 | $R_1, R_2, R_3, R_6 = H$,<br>$R_7 = -CH_2CH_2N(CH_3)_2$<br>$R_4 + R_5 =$ phenyl substituted thiazole<br>$Z_1, Z_2 = O$ | 229-230 |

TABLE 1-continued

The structures and melting points of compound 1-34

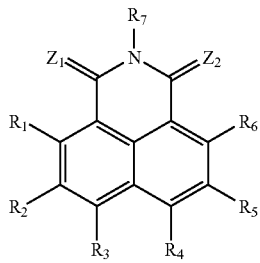

| NO. | STRUCTURE FORMULA | R; $Z_1$, $Z_2$ | M.P. (° C.) |
|---|---|---|---|
| 8 | | $R_1, R_2, R_3, R_6 = H$, $R_7 = -CH_2CH_2N(CH_3)_2$, $R_4 + R_5$ = phenyl substituted thiazole, $Z_1, Z_2 = O$ | 240-241 |
| 9 | | $R_1, R_2, R_3, R_6 = H$, $R_7 = -CH_2CH_2N(CH_3)_2$, $R_4 + R_5$ = phenyl substituted thiazole, $Z_1, Z_2 = O$ | 216-217 |
| 10 | | $R_1, R_2, R_3, R_6 = H$, $R_7 = -CH_2CH_2N(CH_3)_2$, $R_4 + R_5$ = phenyl substituted thiazole, $Z_1, Z_2 = O$ | 235-237 |
| 11 | | $R_1, R_2, R_3, R_6 = H$, $R_7 = -CH_2CH_2N(CH_3)_2$, $R_4 + R_5$ = thiodiazole, $Z_1, Z_2 = O$ | 178-179 |
| 12 | | $R_1, R_2, R_3, R_6 = H$, $R_7 = -CH_2CH_2CH_2CH_3$, $R_4 + R_5$ = thiodiazole, $Z_1, Z_2 = O$ | 177-179 |

TABLE 1-continued

The structures and melting points of compound 1-34

| NO. | STRUCTURE FORMULA | R; $Z_1$, $Z_2$ | M.P. (° C.) |
|---|---|---|---|
| 13 | | $R_1, R_2, R_3, R_6 = H$,<br>$R_7 = -CH_2CH_2CH_2N(CH_3)_2$<br>$R_4 + R_5 = $ thiodiazole<br>$Z_1, Z_2 = O$ | 101-102 |
| 14 | | $R_1, R_2, R_3, R_6 = H$,<br>$R_7 = -CH_2CH_2N\overset{\frown}{\underset{\smile}{N}}NH$;<br>$R_4 + R_5 = $ thiodiazole<br>$Z_1, Z_2 = O$ | 145-146 |
| 15 | | $R_1, R_2, R_3, R_6 = H$,<br>$R_7 = -CH_2CH_2CH_2CH_3$<br>$R_4 + R_5 = $ benzothiophene<br>$Z_1, Z_2 = O$ | 170-172 |
| 16 | | $R_1, R_2, R_3, R_6 = H$,<br>$R_7 = -CH_2CH_2N(CH_3)_2$<br>$R_4 + R_5 = $ benzothiophene<br>$Z_1, Z_2 = O$ | 171-173 |
| 17 | | $R_1, R_2, R_3, R_6 = H$,<br>$R_7 = -CH_2CH_2N\overset{\frown}{\underset{\smile}{N}}NH$;<br>$R_4 + R_5 = $ benzothiophene<br>$Z_1, Z_2 = O$ | 226-228 |

TABLE 1-continued

The structures and melting points of compound 1-34

| NO. | STRUCTURE FORMULA | R; $Z_1$, $Z_2$ | M.P. (° C.) |
|---|---|---|---|
| 18 | | $R_1$, $R_2$, $R_3$, $R_6$ = H,<br>$R_7$ = —$CH_2CH_2CH_2N(CH_3)_2$<br>$R_4$ + $R_5$ = benzothiophene<br>$Z_1$, $Z_2$ = O | 168-170 |
| 19 | | $R_1$, $R_2$, $R_3$, $R_6$ = H,<br>$R_7$ = —$CH_2CH(OOH)C(=CH_2)CH_3$<br>$R_4$ + $R_5$ = benzothiophene<br>$Z_1$, $Z_2$ = O | 174-175 |
| 20 | | $R_1$, $R_2$, $R_3$, $R_6$ = H,<br>$R_7$ = —$CH_2CH(OH)C(=CH_2)CH_3$<br>$R_4$ + $R_5$ = benzothiophene<br>$Z_1$, $Z_2$ = O | 95-97 |
| 21 | | $R_1$, $R_2$, $R_3$, $R_6$ = H,<br>$R_7$ = —$CH_2CH=CH(CH_3)_2$<br>$R_4$ + $R_5$ = benzothiophene<br>$Z_1$, $Z_2$ = O | 207-208 |
| 22 | | $R_1$, $R_2$, $R_5$, $R_6$ = H,<br>$R_7$ = —$CH_2CH_2CH(OOH)C(=CH_2)CH_3$<br>$R_3$ + $R_4$ = heteroaromatic fused ring<br>$Z_1$, $Z_2$ = O | 210-211 |

TABLE 1-continued

The structures and melting points of compound 1-34

| NO. | STRUCTURE FORMULA | R; Z₁, Z₂ | M.P. (° C.) |
|---|---|---|---|
| 23 | | $R_1, R_2, R_5, R_6 = H$,<br>$R_7 = -CH_2CH_2CH=CH(CH_3)_2$<br>$R_3 + R_4$ = heteroaromatic fused ring<br>$Z_1, Z_2 = O$ | 202-203 |
| 24 | | $R_1, R_2, R_3, R_4, R_5, R_6 = H$,<br>$R_7 = -OCOC_6H_5$;<br>$Z_1 = S; Z_2 = O$ | 189-190 |
| 25 | | $R_1, R_2, R_3, R_4, R_5, R_6 = H$,<br>$R_7 = -OCOC_6H_4(p-F)$;<br>$Z_1 = S; Z_2 = O$ | 186-187 |
| 26 | | $R_1, R_2, R_3, R_4, R_5, R_6 = H$,<br>$R_7 = -OCOC_6H_4(p-Cl)$;<br>$Z_1 = S; Z_2 = O$ | 182-183 |
| 27 | | $R_1, R_2, R_3, R_4, R_5, R_6 = H$,<br>$R_7 = -OCOC_6H_4(p-CH_3)$;<br>$Z_1 = S; Z_2 = O$ | 204-205 |
| 28 | | $R_1, R_2, R_3, R_4, R_5, R_6 = H$,<br>$R_7 = -OCOC_6H_4(p-OCH_3)$;<br>$Z_1 = S; Z_2 = O$ | 200-201 |

TABLE 1-continued

The structures and melting points of compound 1-34

| NO. | STRUCTURE FORMULA | R; $Z_1$, $Z_2$ | M.P. (° C.) |
|---|---|---|---|
| 29 | | $R_1, R_2, R_3, R_4, R_5, R_6 = H$, $R_7 = -OCOC_6H_3(m-Cl)_2$; $Z_1 = S; Z_2 = O$ | 212-214 |
| 30 | | $R_1, R_2, R_3, R_4, R_5, R_6 = H$, $R_7 = -OCOC_6H_3(p-Cl, o-F)$; $Z_1 = S; Z_2 = O$ | 208-210 |
| 31 | | $R_1, R_2, R_3, R_4, R_5, R_6 = H$, $R_7 = -OCOC_6H_3(m-CH_3)_2$; $Z_1 = S; Z_2 = O$ | 216-218 |
| 32 | | $R_1, R_2, R_3, R_4, R_5, R_6 = H$, $R_7 = -OCOC_6H_3(p-OCH_3, m-OCH_3)$; $Z_1 = S; Z_2 = O$ | 221-223 |
| 33 | | $R_1, R_2, R_3, R_4, R_5, R_6 = H$, $R_7 = -OCOC_6H_5(m-Cl)$; $Z_1 = S; Z_2 = O$ | 210-212 |
| 34 | | $R_1, R_2, R_3, R_4, R_5, R_6 = H$, $R_7 = -OCOC_4H_3O$ $Z_1 = S; Z_2 = O$ | 209-211 |

EXAMPLE 35

In Vitro Inhibition of Cancer Cell Growth

The cell growth inhibition of mice leukemia cell P388 was evaluated by MTT (microculture tetrozolium) assay, while the cell growth inhibition of human lung adenocarcinoma cell A-549 was evaluated by SRB (Sulforhodamine B) protein staining assay.

The procedure of MTT assay was as follows: appropriate amount of cells in log phase were seeded in 96-well plates (6000 cells/well, 15000 cells/well, 90ul/well) according to the growing rate. After cultured for 24 h, cells were exposed to serial dilutions of drugs in triplicate (10 ul/well). In addition, wells without cell, and wells without cell but with serial dilutions of drugs in case of using a colored-drug were set for zeroing. Then, the cells were cultured in 5% $CO_2$ humidified incubator at 37° C. for 48 h. After treatment of drugs for 48 h, 20ul MTT (Sigma) which was diluted by normal saline to the concentration of 5 mg/ml was added to each well, 50ul/well 10%SDS-5% isobutanol-0.01% mol/LHCl was added after 4 h. After cultured overnight, absorbance was measured at 570 nm using a multiwell spectrophotometer. The inhibition effect of the compounds in test (percentage of growth inhibition) was calculated for each well:

% inhibition=$(OD570_{control\ cells} - OD570_{treated\ cells})/OD570_{control\ cells} \times 100\%$.

The procedure of SRB assay was as follows: appropriate amount of cells in log phase were seeded in 96-well plates according to the growing rate (90 ul/well). After cultured for 24 h, cells were exposed to serial dilutions of drugs in triplicate (10 ul/well). In addition, control wells of normal saline in corresponding concentrations and zeroing wells without cell were set. The cells were incubated in 5% $CO_2$ humidified incubator at 37° C. After 72 h, the medium was removed and cells were fixed with cold 10% trichloric acid (TCA) at 4° C. for 1 h. The plates were washed with distilled water 5 times, and stained in room temperature with 4 mg/ml SRB (Sigma, diluted with 1% glacial acetic acid, 100 ul/well) for 15 minutes after air drying. SRB was then washed with 1% acetic acid 5 times. Plates were dried, followed by adding 150 ul/well Tris solution. Absorbance was measured at 520 nm using a multiwell spectrophotometer. The inhibition effect of the compounds in test (percentage of growth inhibition) was calculated for each well:

% inhibition=$(A540_{control\ cells} - A540_{treated\ cells})/A540_{control\ cells} \times 100\%$.

The methods used were MTT assay or SRB assay.

The cell lines used were mice leukemia cell P388, human leukemia cell MOLT-4, human lung adenocarcinoma cell A-549, human gastric adenocarcinoma SGC-7901, human hepatocellular carcinoma BEL-7402 and human embryonal fibroblast WI-38 (commerially available from ATCC).

The exposure time to compounds was 48 h-72 h.

The in vitro cell growth inhibition of compounds 1-18 was listed below.

TABLE 2

Growth inhibition effect of compounds to A-549 cell strain (%)

| Samples | Concentration (M) | | | | |
|---|---|---|---|---|---|
| | $10^{-4}$ | $10^{-5}$ | $10^{-6}$ | $10^{-7}$ | $10^{-8}$ |
| compound 1 | 34.4 | 0 | 0 | 0 | 0 |
| compound 2 | 91.3 | 90.2 | 75.1 | 50.2 | 16.9 |
| compound 3 | 78.6 | 92.4 | 69.8 | 4.7 | 0 |
| compound 4 | 80.3 | 92.9 | 73.5 | 33.4 | 17.3 |
| compound 5 | 94.8 | 91.5 | 73.0 | 69.7 | 17.8 |
| compound 6 | 95.8 | 92.3 | 52.7 | 31.5 | 7.1 |
| compound 7 | 89.1 | 89.0 | 72.3 | 71.3 | 52.0 |
| compound 8 | 95.2 | 59.6 | 18.6 | 1.0 | 0.2 |
| compound 9 | 94.9 | 93.9 | 94.5 | 69.4 | 44.5 |
| compound 10 | 91.4 | 93.4 | 94.5 | 35.7 | 12.5 |
| compound 11 | 95.7 | 93.7 | 94.5 | 76.6 | 20.2 |
| compound 12 | 69.4 | 75.2 | 0 | 2.3 | 0 |
| compound 13 | 95.9 | 94.4 | 90.6 | 0 | 0 |
| compound 14 | 95.9 | 96.1 | 87.3 | 60.2 | 4.4 |
| compound 15 | 94.0 | 45.6 | 0 | 0 | 0 |
| compound 16 | 97.1 | 96.6 | 85.2 | 72.2 | 55.3 |
| compound 17 | 91.1 | 95.4 | 46.8 | 0 | 1.7 |
| compound 18 | 95.3 | 96.9 | 81.1 | 47.2 | 1.7 |

TABLE 3

Growth inhibition effect of compounds to MOLT-4 cell strain (%)

| Samples | Concentration (M) | | | | |
|---|---|---|---|---|---|
| | $10^{-4}$ | $10^{-5}$ | $10^{-6}$ | $10^{-7}$ | $10^{-8}$ |
| compound 1 | 100 | 98.5 | 97.7 | 77.4 | 1.1 |
| compound 2 | 100 | 100 | 97.7 | 42.3 | 0 |
| compound 4 | 100 | 99.7 | 93.9 | 22.3 | 0 |
| compound 7 | 95.1 | 99.2 | 100 | 13.3 | 0 |
| compound 11 | 100 | 100 | 100 | 82.8 | 0 |

TABLE 4

Growth inhibition effect of compounds to SGC-7901 cell strain (%)

| Samples | Concentration (M) | | | | |
|---|---|---|---|---|---|
| | $10^{-4}$ | $10^{-5}$ | $10^{-6}$ | $10^{-7}$ | $10^{-8}$ |
| compound 1 | 87.5 | 56.2 | 46.0 | 21.4 | 9.8 |
| compound 2 | 96.2 | 88.0 | 37.8 | 28.5 | 0.8 |
| compound 4 | 94.5 | 91.8 | 39.1 | 0.2 | 13.8 |
| compound 7 | 96.4 | 95.1 | 67.0 | 6.9 | 3.4 |
| compound 11 | 96.5 | 97.1 | 38.9 | 16.7 | 1.1 |

TABLE 5

Growth inhibition effect of compounds to BEL-7402 cell strain (%)

| Samples | Concentration (M) | | | | |
|---|---|---|---|---|---|
| | $10^{-4}$ | $10^{-5}$ | $10^{-6}$ | $10^{-7}$ | $10^{-8}$ |
| compound 1 | 70.1 | 76.9 | 67.0 | 3.7 | 6.6 |
| compound 2 | 95.1 | 90.7 | 72.9 | 24.9 | 14.2 |
| compound 4 | 94.6 | 95.0 | 50.7 | 24.3 | 17.9 |
| compound 7 | 96.9 | 95.8 | 80.6 | 33.1 | 17.0 |
| compound 11 | 95.7 | 90.9 | 74.0 | 20.1 | 24.4 |

TABLE 6

Growth inhibition effect of compounds to P388 cell strain (%)

| Samples | Concentration (M) | | | | |
|---|---|---|---|---|---|
| | $10^{-4}$ | $10^{-5}$ | $10^{-6}$ | $10^{-7}$ | $10^{-8}$ |
| compound 1 | 51.7 | 10.2 | 6.4 | 2.2 | 4.3 |
| compound 2 | 99.9 | 78.9 | 22.2 | 7.7 | 10.1 |
| compound 3 | 100 | 100 | 22.2 | 0 | 0 |
| compound 4 | 100 | 100 | 23.1 | 11.0 | 16.2 |
| compound 5 | 96.6 | 87.7 | 48.2 | 21.1 | 8.1 |
| compound 6 | 96.0 | 74.7 | 47.7 | 29.3 | 13.0 |
| compound 7 | 98.7 | 74.6 | 47.9 | 15.8 | 18.0 |
| compound 8 | 94.8 | 45.9 | 24.9 | 10.0 | 8.8 |
| compound 9 | 95.1 | 92.3 | 78.2 | 15.2 | 21.0 |
| compound 10 | 96.1 | 89.0 | 64.6 | 40.5 | 7.3 |
| compound 11 | 98.7 | 92.7 | 42.2 | 13.8 | 10.7 |
| compound 12 | 54.3 | 23.2 | 17.1 | 12.3 | 15.6 |
| compound 13 | 99.5 | 89.2 | 19.8 | 11.0 | 14.5 |
| compound 14 | 98.8 | 90.8 | 16.8 | 13.7 | 18.4 |
| compound 15 | 51.8 | 26.0 | 3.2 | 3.2 | 5.8 |
| compound 16 | 100 | 95.9 | 68.2 | 21.4 | 13.8 |
| compound 17 | 100 | 100 | 23.9 | 4.5 | 2.0 |
| compound 18 | 100 | 100 | 29.8 | 17.1 | 5.5 |

This result showed that these compounds were potent against tumor cells, especially active against human lung cancer cells, human stomach cancer cells, human hepatoma cancer cells and leukemia cells. The inhibition of cell growth was significantly dose dependent.

EXAMPLE 36

In Vivo Anti-tumor Activity

The compounds to be tested were compound 7, 9 and 16 (C7, C9 and C16).

S-180 sarcoma developed for 7-11 days and in good growth trend was homogenated into cell suspension. The cell suspension was inoculated subcutaneously into right armpit of female KM mice (18~22 g) (about $1.0-2.5\times10^6$ cells/mouse). After 24 h, the mice were grouped in random with compounds administrated by i.p. injection. From the next day on, the mice were given serial dosages. After treatment, animals were killed, and solid tumors were removed and weighed after the body weight were weighed. The inhibition rate was calculated as follows, and T-test was carried out:

[(Average tumor weight of NS group−Average tumor weight of test group)/Average tumor weight of NS group]×100%.

Result of Inhibition of Tumor Growth in Mice

It can be seen from the results that compound 16 (C16) was active against mice S180 sarcoma, while Amonafide, C7 and C9 were not potent against the mice S180 sarcoma. In S180 sarcoma model, C16 at i.p. doses from 12.5, 25 to 50 mg/kg were administered and the dose-dependent tumor inhibition rate was 29.6%, 71.6% and 95.6%, respectively. The tumor inhibition rate of 50 mg/kg C16 was equivalent to the reference compound 5-FU (see table 7). As for $H_{22}$ hepatoma, C16 at i.p. doses of 15 mg/kg and 30 mg/kg was administered, and the dose-dependently tumor inhibition rate was 51.0% and 72.6%, respectively, but was not active at the dose of 7.5 mg/kg. Amonafide was not as active in parallel experiments. C7 and C9 were active against S180 sarcoma, but weaker than C16.

TABLE 7

Tumor growth inhibition of C16 to mice S-180 sarcoma

| Group | Dosage | route of administration | Numbers of mice | | Weight of mice (g) | | Weight of tumor (g) | Tumor growth inhibition % | P |
|---|---|---|---|---|---|---|---|---|---|
| | | | Day 1 | Day 7 | Day 1 | Day 7 | mean ± SD | | |
| NS | — | | 20 | 20 | 19.8 | 32.1 | 1.62 ± 0.49 | — | — |
| C16 | 50 mg/kg* | i.p | 10 | 10 | 19.6 | 12.9 | 0.08 ± 0.04 | 95.6 | <0.01 |
| C16 | 25 mg/kg | i.p | 10 | 10 | 19.7 | 18.6 | 0.46 ± 0.24 | 71.6 | <0.01 |
| C16 | 12.5 mg/kg | i.p | 10 | 10 | 19.9 | 26.9 | 1.14 ± 0.29 | 29.6 | <0.05 |
| Amonafide | 10 mg/kg | i.p | 10 | 10 | 19.7 | 31.3 | 1.37 ± 0.26 | 15.4 | >0.05 |
| Amonafide | 5 mg/kg | i.p | 10 | 10 | 19.6 | 32.0 | 1.12 ± 0.35 | 30.9 | <0.01 |
| 5-FU** | 75 mg/kg | i.v | 10 | 10 | 19.6 | 20.7 | 0.05 ± 0.04 | 96.9 | <0.01 |

*After administrate C16 by i.p. in a dosage of 50 mg/kg 4 times, 8 mice were dead on Day 7;
**5-FU was injected twice (Day 1 and Day 4).

These results showed that the compounds of the invention displayed an excellent in vivo anti-tumor activity. Further studies showed that C16 as well as Amonafide could arrest tumor cell cycle in G2/M phase (significantly dose-dependent), trigger tumor cell apoptosis, impact directly on DNA and induce the broken of DNA double strand. To sum up, these activities C16 displayed were much stronger than those of Amonafide. Importantly, as for C16, the acetylation site (presented in Amonafide and lead to in vivo toxic after metabolism) substituted by a heterocycle, thus avoiding the N-acetylation that may lead to internal toxic.

All the documents cited herein are incorporated into the invention as reference, as if each of them is individually incorporated. Further, it would be appreciated that, in the above teaching of invention, the skilled in the art could make certain changes or modifications to the invention, and these

The invention claimed is:

1. A compound of formula (Ia):

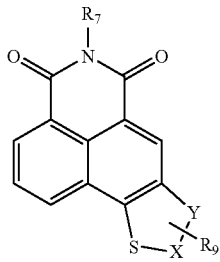

wherein $R_7$ is $C_1$-$C_6$ alkyl, —($C_1$-$C_6$ alkyl)—$NH_2$, —($C_1$-$C_6$ alkyl)$N(C_1$-$C_6$ alkyl$)_2$, or —($C_1$-$C_6$ alkyl)piperazine;
wherein X and Y are independently C or N;
wherein $R_9$ is a phenyl, or a phenyl substituted by 1-3 substituents, wherein the substituents are $C_1$-$C_6$ alkyl, —$NO_2$, —OH, $C_1$-$C_6$ alkoxy, or halo, or $R_9$ taken together with X and Y form a benzene ring;
with the proviso that $R_9$ is absent when X=Y=N; and provided R7 is not a C1-C6 alkyl when R9 taken together with X and Y form a benzene ring
or pharmaceutically acceptable salts thereof.

2. The compound of claim 1, wherein $R_9$ taken together with X and Y form a benzene ring, and $R_7$ is —($C_1$-$C_6$ alkyl)$N(C_1$-$C_6$ alkyl$)_2$.

3. The compound of claim 1, wherein the compound is:

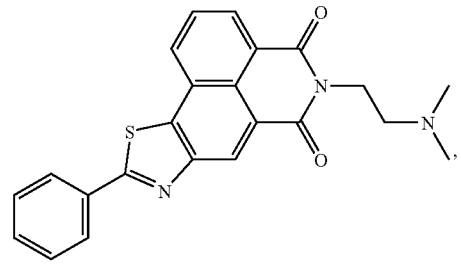

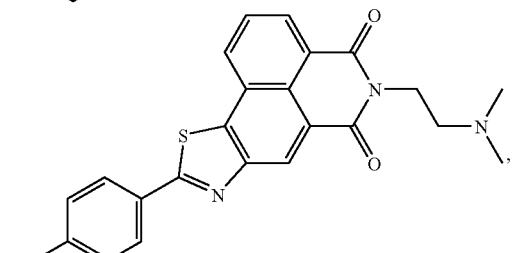

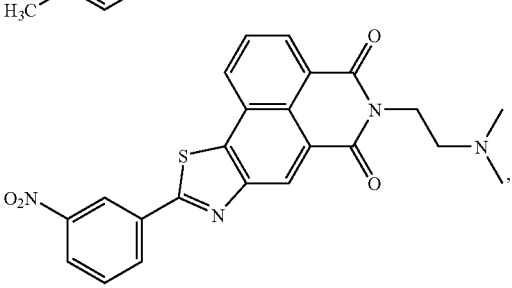

-continued

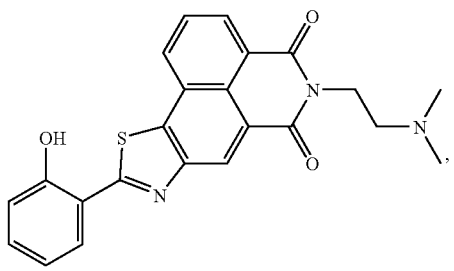

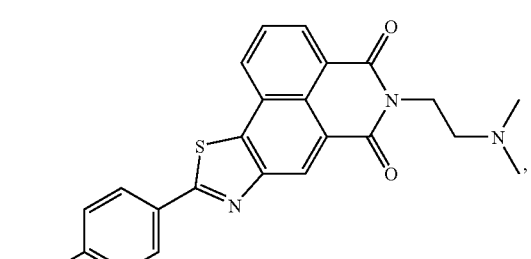

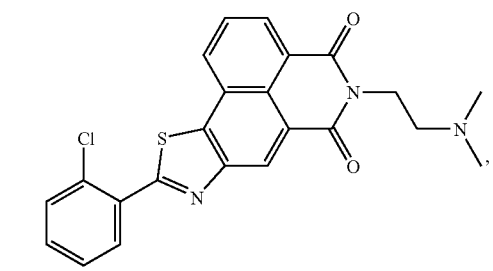

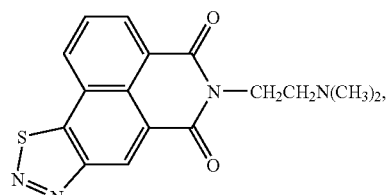

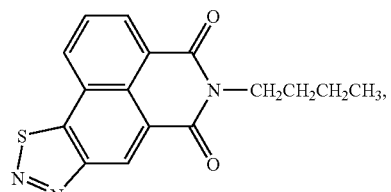

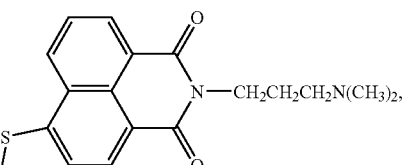

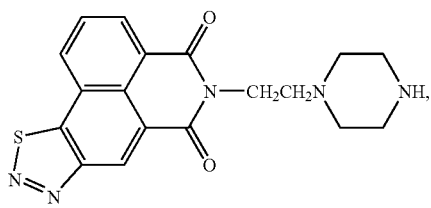

4. A pharmaceutical composition comprising: a compound of formula (Ia):

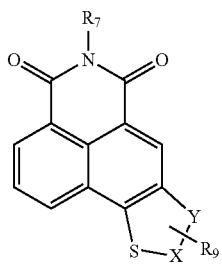

(Ia)

wherein $R_7$ is $C_1$-$C_6$ alkyl, —($C_1$-$C_6$ alkyl)—$NH_2$, —($C_1$-$C_6$ alkyl)N($C_1$-$C_6$ alkyl)$_2$, or —($C_1$-$C_6$ alkyl) piperazine;

wherein X and Y are independently C or N;

wherein $R_9$ is a phenyl, or a phenyl substituted by 1-3 substituents, wherein the substituents are $C_1$-$C_6$ alkyl, —$NO_2$, —OH, $C_1$-$C_6$ alkoxy, or halo, or $R_9$ taken together with X and Y form a benzene ring;

with the proviso that $R_9$ is absent when X=Y=N; and provided R7 is not a C1-C6 alkyl when R9 taken together with X and Y form a benzene ring or pharmaceutically acceptable salts thereof; and a pharmaceutically acceptable carrier or excipient.

* * * * *